(12) United States Patent
Taneja

(10) Patent No.: US 8,946,258 B1
(45) Date of Patent: Feb. 3, 2015

(54) METHODS OF NON-GASTROINTESTINAL ENDOSCOPIC PROCEDURES USING L-HYOSCYAMINE ORAL FORMULATIONS

(71) Applicant: Jugal K. Taneja, Tampa, FL (US)

(72) Inventor: Jugal K. Taneja, Tampa, FL (US)

( * ) Notice: Subject to any disclaimer, the term of this patent is extended or adjusted under 35 U.S.C. 154(b) by 0 days.

(21) Appl. No.: 13/965,819

(22) Filed: Aug. 13, 2013

Related U.S. Application Data

(63) Continuation-in-part of application No. 12/931,784, filed on Feb. 10, 2011, now abandoned.

(51) Int. Cl.
 *A61K 31/44* (2006.01)
 *A61K 9/00* (2006.01)
 *A61K 31/46* (2006.01)

(52) U.S. Cl.
 CPC .................................. *A61K 31/46* (2013.01)
 USPC .......................................... 514/304; 424/400

(58) Field of Classification Search
 USPC .......................................... 514/304; 424/400
 See application file for complete search history.

(56) References Cited

U.S. PATENT DOCUMENTS

2007/0202167 A1 * 8/2007 Srinivasan et al. ............ 424/468

FOREIGN PATENT DOCUMENTS

WO    WO 2002/20005    *    3/2002

OTHER PUBLICATIONS

Gronnebech et al. "Glycopyrrolate vs. atropine during anaesthesia for Laryngoscopy and bronchoscopy," Acta Anaesthesiologica Scandinavica, 1993, vol. 37, No. 5, pp. 454-457, Medline Abstract, Accession No. 1993362492.*
Chaptini et al. "Sublingual Hyposcyamine spray as premedication for colonoscopy: a randomized double-blinded placebo-controlled trial," The American Journal of Surgery, 2008, vol. 196, pp. 61-56.*

* cited by examiner

*Primary Examiner* — Shengjun Wang

(57) ABSTRACT

Methods of performing non-gastrointestinal endoscopic procedures with concomitant dosing with rapidly disintegrating oral formulations of single active ingredient L-Hyoscyamine rapidly dissolving tablets.

16 Claims, No Drawings

METHODS OF NON-GASTROINTESTINAL ENDOSCOPIC PROCEDURES USING L-HYOSCYAMINE ORAL FORMULATIONS

RELATED APPLICATION

The present application ids a continuation-in-part of pending U.S. patent application Ser. No. 12/931,784 filed Feb. 10, 2011, the subject matter of which is incorporated herein by reference.

FIELD OF THE INVENTION

The present invention relates to novel methods of performing endoscopic procedures outside of the gastrointestinal tract by using rapidly disintegrating oral formulations of L-Hyoscyamine.

SUMMARY OF THE INVENTION

Endoscopy is generally a non-surgical procedure whereby an instrument, called an endoscope, and preferably a flexible endoscope, is inserted directly into a bodily cavity, or inserted through an incision of an organ or tissue, to visually examine, and take computer-aided images, of the interior of an organ tissue or cavity. Frequently the purpose of endoscopy is to examine a tissue region suspected of having a lesion, or to examine the lesion more closely. Lesions may include areas of inflammation, tumor growth, and ulcer formation. The area around the lesion, or the lesion itself, frequently forms secretions that make visualization and imaging with endoscopy difficult. The motility of tissue along with muscular and visceral spasms can make advancing the endoscope difficult, or can result in tissues obstructing both visualization and imaging with the endoscope. It is desirable to improve the procedure of endoscopy with a method of reducing tissue and muscle motility, drying secretions, and reducing spasms to enhance visibility and imaging during endoscopic procedures of narrow tissues and cavities, preferably tissues outside of the gastrointestinal tract. The present invention of novel methods satisfies this need.

The pharmaceutical use of anticholinergic agents for the treatment of numerous medical conditions is well known in the prior art. The terms "anticholinergic agent" or "anticholinergics" refer to substances that oppose the action of the neurotransmitter acetylcholine. Acetylcholine is an essential neurotransmitter in both the central nervous system, where it functions as a neuromodulator in the brain, and in the peripheral nervous system, where it plays an important role in skeletal muscle contraction, along with autonomic function; the involuntary control of internal organs and glands. Acetylcholine, therefore, affects cognitive function, as well as, salivation, perspiration, pupil dilation, urination, heart rate, respiration, sexual arousal, and digestion. The actions of acetylcholine are modulated by two main classes of receptors, nicotinic acetylcholine receptors and muscarinic acetylcholine receptors. Nicotinic acetylcholine receptors are involved in voluntary skeletal muscle contraction, while muscarinic acetylcholine receptors effect secretory exocrine glands, smooth muscle and the cardiac muscle.

Atropine is perhaps one of the earliest known anticholinergic agents, and serves as a competitive antagonist for the muscarinic acetylcholine receptor, and is considered an antimuscarinic agent. Atropine is a secondary metabolite produced by most members of the flowering plant family Solanaceae. The extracts of plants containing atropine, such as *Mandragora officinarum* and *Atropa belladona*, also called deadly nightshade, have been used for at least two thousand years as an anesthetic for treating pain from wounds and gout, as well as, for treating sleeplessness. Atropine has also been used for dilating pupils and for surgical anesthesia.

Atropine is a natural tropane alkaloid extract from plants of the family Solanaceae, which consists of a racemic mixture of the isomeric tropane alkaloids, D-hyoscyamine and L-hyoscyamine. L-hyoscyamine has the Chemical Abstracts Service (CAS) name of [3(S)-endo]-α-(Hydroxymethyl) benzeneacetic acid 8-methyl-8-azabicyclo[3.2.1]oct-3-yl ester, and may be chemically synthesized rather than extracted. The present invention pertains to single active pharmaceutical ingredient oral formulations of L-Hyoscyamine and not formulations containing atropine or D-Hyoscyamine.

Oral tablets of L-Hyoscyamine in the form of a sulfate salt are primarily used for treating gastrointestinal disorders. L-Hyoscyamine Sulfate is indicated as adjunctive therapy in the treatment of peptic ulcers. It can also be used to control gastric secretion, visceral spasm and hypermotility in spastic colitis, spastic bladder, cystitis, pylorospasm, and associated abdominal cramps. L-Hyoscyamine Sulfate may also be used in functional intestinal disorders to reduce symptoms such as those seen in mild dysenteries, diverticulitis, and acute enterocolitis. L-Hyoscyamine Sulfate is used as adjunctive therapy in the treatment of irritable bowel syndrome (irritable colon, spastic colon, mucous colitis), neurogenic bowel disturbances, and functional gastrointestinal disorders. Hyoscyamine Sulfate is also indicated along with morphine or other narcotics in symptomatic relief of biliary and renal colic.

Other more seldom uses of L-Hyoscyamine Sulfate include use as a drying agent in the relief of symptoms of acute rhinitis; in the therapy of parkinsonism to reduce rigidity and tremors and to control parkinsonism associated siallorrhea and hyperhidrosis, excessive drooling and sweating. L-Hyoscyamine Sulfate may also be used in the therapy of poisoning by anticholinesterase agents.

The present invention provides novel methods of performing non-gastrointestinal endoscopic procedures with concomitant dosing with rapidly disintegrating oral formulations of L-Hyoscyamine, and preferably rapidly dissolving L-Hyoscyamine Sulfate tablets. Oral dosing with single-active ingredient L-Hyoscyamine has never before been provided concomitantly to an endoscopic procedure outside of the gastrointestinal tract, and is believed to have been tried only once with the gastrointestinal tract during sigmoidoscopy of the large intestine to reduce patient discomfort, but was not found effective. Since L-hyoscyamine is primarily used for treating the gastrointestinal tract, its concomitant use in endoscopic procedures in non-gastrointestinal tissues is novel and non-obvious.

The Applicant has found that single-active ingredient, oral formulations of L-Hyoscyamine Sulfate can unexpectedly aid other endoscopic procedures, including bronchoscopy (of the lower respiratory tract), rhinoscopy (of the nose), laryngoscopy (of the vocal cords), and cystoscopy (of the urinary tract). The present invention can also improve endoscopic procedures that require an incision to access closed body cavities and organ tissues, including laparoscopy of the abdominal and pelvic cavities, arthroscopy of a joint, and thoracoscopy of the chest cavity. The present invention can also have uses in endoscopy of the heart and blood vessels, coronary endoscopy, including arteries and veins, and even lymphatic vessels or nodes.

The Applicant had discovered these uses by exploring the actions of L-Hyoscyamine on the inhibition of tissue motility and spasms and drying of secretions in these non-gastrointestinal organ systems. Secretions include mucous and discharge of other bodily fluids, and may be accompanied by saliva.

Saliva glands have ducts and are classified as exocrine glands. There are five major salivary glands, along with over 600 minor salivary glands located throughout the oral mucosa of the oral cavity. Saliva glands and their saliva flow output are under the unconscious control of the autonomic nervous system, including that of the parasympathetic nervous system that regulates resting bodily functions. Here, the anticholinergic L-Hyoscyamine, administered orally or sublingually, can antagonize the muscarinic acetylcholine receptors of postganglionic cholinergic nerves that would otherwise stimulate excessive saliva secretion in these glands. However, there are other bodily secretions and discharges that can be influenced by L-Hyoscyamine.

The Applicant has found that single-active ingredient L-Hyoscyamine orally dosed can improve these endoscopic procedures in three main ways: by decreasing motility for improved advancement of the endoscopic instrument through the organ or vessel being studied; improving visibility by decreasing bodily secretions in or around the organ or vessel being studied; and by improving visualization around a suspected lesion as an antispasmodic by relaxing and flattening any bulges or folds in or around the suspected lesion. These newly discovered methods also have great significance for endoscopic imaging techniques including narrow band imaging and optical coherence tomography. Narrow band imaging uses different wavelengths of light to enhance the detail of the tissue under endoscopic study. Optical coherence tomography captures micrometer-resolution, three-dimensional images using long wavelength light and by penetrating tissue being studied, which serves as an optical scattering media. Optical coherence tomography generally requires more time in optical signal acquisition and processing, so that L-Hyoscyamine can keep the tissue still and free of secretions during this endoscopic imaging technique.

There remains a need for improved access, visibility, and imaging capture in endoscopic procedures of narrow tissues. The present invention provides novel methods of performing non-gastrointestinal endoscopic procedures with concomitant dosing with rapidly disintegrating oral formulations of single active ingredient L-Hyoscyamine, and preferably rapidly dissolving L-Hyoscyamine Sulfate tablets, to satisfy that need.

DESCRIPTION OF THE PRIOR ART

Methods of preparing and administering compositions of anticholinergic agents, such as L-hyoscyamine, to treat a myriad of illnesses is known in the prior art.

By way of example, U.S. Pat. Appl. No. 20090258848 describes biomarkers for inflammatory bowel disease and includes a method of qualifying inflammatory bowel disease status and administering one or more of a multitude of therapeutic agents, one of which includes hyoscyamine.

U.S. Pat. Nos. 4,443,428 and 4,861,598 describe a slow, controlled release pharmaceutical composition using a hydrophobic matrix available for oral ingestion, of which, hyoscyamine can be one of the active substances.

U.S. Pat. Nos. 5,785,989 and 5,288,497 describe a dissolvable matrix made from carbohydrate, fat, protein, or lipid that can hold a pharmaceutically active ingredient, such as atropine, for transmucosal oral and sublingual delivery using a lollipop-like holder or appliance to administer the drug to the mouth.

U.S. Pat. No. 6,197,801 describes an injectable pharmaceutical composition for the treatment of erectile dysfunction, consisting of prostaglandin E-1 and Levsin, and other vasodilators, which may include hyoscyamine.

U.S. Pat. No. 6,814,955 describes the systemic delivery of a number of different biologically relevant molecules, including hyoscyamine, by aerosol administration via the inhalation route.

U.S. Pat. No. 7,816,396 describes a method of treating sialorrhea by orally administering a liquid solution of the anticholinergic glycopyrrolate. But, glycopyrrolate has been known to reduce the activity of the salivary gland, to reduce salivation, since the 1960s (Juniper, 1967, "The relative effect of an anticholinergic drug, glycopyrrolate, on basal gastric secretion and sweat- and salivary-gland activity").

U.S. Pat. Appl. No. 20060128637 describes the process of making phenolic acid complexes of hyoscyamine, hyoscyamine tannate, for pharmaceutical use with slower absorption characteristics.

U.S. Pat. Appl. No. 20070190142 describes a formulation of a number of different drugs using an alkacrylate polymer.

U.S. Pat. Appl. No. 20070202167 describes a pharmaceutical dosage form of ingested hyoscyamine comprising two or more formulations of hyoscyamine, including at least one immediate release formulation and at least one controlled released formulation, in effort to yield a plasma concentration of hyoscyamine capable of achieving systemic effects. However, this application does not describe an orally disintegrating dosage form of hyoscyamine, and therefore, this dosage is not suited for buccal absorption via sublingual administration, and therefore, onset is not presumed to be rapid, and the hyoscyamine can be subject to first-pass metabolism.

U.S. Pat. Appl. No. 20070092553 describes compositions and methods of making rapidly dissolving oral drug formulations using a drug-resin complex of microbeads, along with a free-flowing excipient. This application further describes a hyoscyamine-resin complex. However, this formulation is designed so that "hyoscyamine is released slowly when the composition is chewed . . . not fully dissolving for at least 30 seconds when chewed," which will delay onset. Likewise, U.S. Pat. No. 4,996,047 also describes sustained release pharmaceutical compositions using a drug-resin complex, using ion-exchange resins, that can include hyoscyamine, among other drugs. Similarly, U.S. Pat. No. 5,508,043 describes a controlled release matrix made from sodium alginate and a calcium salt.

U.S. Pat. Appl. No. 20040170687 describes a pharmaceutical combination of two reactive ingredients, such as hyoscyamine and phenyl salicylate, wherein at least one of these ingredients is coated, such as with polymeric material, to prevent reactivity between them.

U.S. Pat. Appl. No. 20080102102 describes a method for temporarily decreasing saliva production in an individual with intra-oral administration of any one of a number of different anticholinergic agents, including atropine and hyoscyamine.

It is the goal of the current invention to provide improved access, visibility, and imaging capture in endoscopic procedures, especially of narrow tissues. The present invention provides novel methods of performing non-gastrointestinal endoscopic procedures with concomitant dosing with rapidly disintegrating oral formulations of L-Hyoscyamine, and preferably rapidly dissolving L-Hyoscyamine Sulfate tablets.

Such novel methods can reduce time and cost of an endoscopic procedure, as well as, enhance the visibility and efficacy of the endoscopic procedure.

Before explaining at least one embodiment of the invention in detail, it is to be understood that the invention is not limited in its application to the details of administration set forth in the following description. The invention is capable of other embodiments and of being practiced and carried out in various ways. Also, it is to be understood that the phraseology and terminology employed herein are for the purpose of descriptions and should not be regarded as limiting.

DETAILED DESCRIPTION OF THE INVENTION

The present invention relates to a pharmaceutical composition comprising L-hyoscyamine sulfate and more particularly pertains to novel methods of performing non-gastrointestinal endoscopic procedures with concomitant dosing with rapidly disintegrating oral formulations of rapidly dissolving L-Hyoscyamine Sulfate tablets, although other oral dosage forms can be used including capsules and extended release oral dosage forms.

Preferably, the L-Hyoscyamine oral dosage form is a rapidly dissolving oral tablet, and more preferably a sublingual tablet that dissolves in under 60 seconds and has an onset that begins in less than 15 minutes from administration. This tablet is preferably produced by a dry method of tablet preparation; one that avoids heat drying, solvents and alkalies in solution. The preferred formulation would utilize the method of geometric mixing under cool, dry conditions to avoid the undesired conversion of active L-hyoscyamine into inactive D-hyoscyamine, and the undesired hydrolysis of L-hyoscyamine into tropine and tropic acid. This would ensure that all or nearly all of the L-hyoscyamine stays active and stable, and also ensures dosage uniformity, homogeneity, among tablets.

The preferred formulation of the disintegrable oral tablet is comprised of 0.125 mg of L-Hyoscyamine sulfate, 78.875 mg of mannitol, 20 mg of croscarmellose sodium, and 1 mg of magnesium stearate, although an extra strength dose of 0.250 mg of L-Hyoscyamine sulfate can be formulated and administered as may be desired for a stronger or longer biologic response.

The excipients of this preferred formulation include croscarmellose sodium, spray dried mannitol, and magnesium stearate. The croscarmellose sodium, which is an internally cross-linked sodium caboxymethylcellulose, is used as a disintegrant agent, that expands and dissolves when wetted by bodily fluids, such as saliva, causing the tablet to disintegrate to rapidly release the hyoscyamine for rapid absorption, such as rapid oral absorption by buccal epithelial tissue. The formulation also includes mannitol, which serves as a diluent because L-hyoscyamine sulfate is so potent. Mannitol is a low glycemic sweetener that does not elevate blood glucose levels, and can offset the taste of hyoscyamine. Mannitol provides a pleasurable, mint-like cooling effect when dissolved, which is attributed to its alcohol functional groups. Mannitol also has low hygroscopicity that helps protect the tablet from humid ambient air. The magnesium stearate is added as a lubricant because it has lubricating properties that make the process of tablet punching more efficient.

Other variations of the this formulation may be acceptable to serve the purposes of the present invention.

The oral dosage form of L-Hyoscyamine is preferably single active ingredient L-Hyoscyamine Sulfate tablets containing a single dosage or a double dosage of 0.125 mg of L-Hyoscyamine Sulfate and at least one excipient. A method is provided for the administration of at least one single or double dosage of 0.125 mg of L-Hyoscyamine Sulfate, administered just before, during, or at least prior to completion of at least one non-gastrointestinal endoscopic procedure, including, but not limited to bronchoscopy, rhinoscopy, laryngoscopy, cystoscopy, gynoscopy, laparoscopy, arthroscopy, thorascopy, coronary endoscopy, lymphatic vessel endoscopy, and lymph node endoscopy, for the function of reducing tissue motility, reducing tissue spasms, and drying secretions including saliva, non-saliva secretions, mucous, non-mucous secretions, discharges and other bodily fluids, so that the visualization and imaging of the at least one endoscopic procedure is enhanced. In other instances, this method can also improve and ease the advancement of the endoscope through the tissue or cavity being examined.

A method is also provided for administering a formulation of L-Hyoscyamine Sulfate as an antispasmodic agent to relax and flatten any bulges or folds in or around a suspected lesion, to enhance and unobstruct endoscopic visualization. This method has advantages in narrow tissues and cavities, preferably those outside the gastrointestinal tract.

A method is also provided for administering a formulation of L-Hyoscyamine Sulfate to provide at least one function from reducing tissue motility, reducing tissue spasms, and drying secretions, to enhance endoscopic narrow band imaging so that visualization is clearer and less obstructed over an extended amount of time during imaging and image capture.

A method is also provided for administering a formulation of L-Hyoscyamine Sulfate to provide at least one function from reducing tissue motility, reducing tissue spasms, and drying secretions, to enhance endoscopic optical coherence tomography so that visualization is clearer and less obstructed over an extended amount of time during imaging and image capture.

Narrow band imaging uses different wavelengths of light to enhance the detail of the tissue under endoscopic study; while optical coherence tomography captures micrometer-resolution, three-dimensional images using long wavelength light and by penetrating tissue being studied, which serves as an optical scattering media. Optical coherence tomography generally requires more time in optical signal acquisition and processing, so that L-Hyoscyamine can keep the tissue still and free of secretions during this endoscopy imaging technique.

The method of the present invention also includes the additional steps of checking the target tissue multiple times throughout the endoscopic procedure to ensure that the L-Hyoscyamine is having, and continues to have, the desired pharmacologic effect of reducing tissue motility and drying secretions, before advancing the endoscopic instrument further. If the pharmacologic effect is sufficient, then endoscopy can resume without further dosing of L-Hyoscyamine; but if the pharmacologic effect is insufficient when checked, additional dosing and checking is required before further endoscopic instrument advancement.

Other variations and embodiments of the invention described herein will now be apparent to those of skill in the art without departing from the disclosure of the invention or the coverage of the claims to follow.

What is claimed as being new and desired to be protected by Letters Patent of the United States is as follows:

1. A method of preventing aspiration and atelectasis in a non-collapsed lung of a patient having a collapsed lung and a non-collapsed lung, said method including the step of administering an oral formulation of L-Hyoscyamine, said method including the further step of bronchoscopy combined with an at least one procedure of fine needle injection into a bronchial lesion/tumor.

2. The method of claim 1 whereby said method is applied with a procedure that requires tissue access via an incision.

3. The method of claim 1 whereby said an at least one procedure of fine needle injection into a bronchial lesion/tumor is a procedure of endobronchial intratumoral chemotherapy.

4. The method of claim 1 whereby said an at least one procedure of fine needle injection into a bronchial lesion/tumor is a procedure of tumor ablation using an ablative catheter inside the lung.

5. The method of claim 1 whereby said method further includes the drying of secretions, including saliva, outside a lung so that said secretions do not enter said lung.

6. The method of claim 1 whereby said method further includes the drying of secretions within a lung that do not contain saliva.

7. The method of claim 1 whereby said method further reduces/prevents reflex airway constriction.

8. The method of claim 1 whereby said method further provides bronchodilation.

9. The method of claim 1 whereby said oral formulation of L-Hyoscyamine is chosen from oral formulation dosage forms including tablets.

10. The method of claim 1 whereby said oral formulation of L-Hyoscyamine contains at least one excipient.

11. The method of claim 1 whereby said oral formulation of L-Hyoscyamine contains 0.125 mg of L-Hyoscyamine Sulfate.

12. The method of claim 1 whereby said oral formulation of L-Hyoscyamine contains 0.250 mg of L-Hyoscyamine Sulfate.

13. The method of claim 1 whereby said oral formulation of L-Hyoscyamine is comprised of 0.125 mg L-Hyoscyamine sulfate, 78.875 mg of mannitol, 20 mg of croscarmellose sodium, and 1 mg of magnesium stearate.

14. The method of claim 1 whereby said method also improves and eases advancement of the endoscope through the lung tissue or cavity being examined.

15. The method of claim 1 whereby said method further enhancing and unobstructing bronchoscopic visualization, said method including the step of administering said oral formulation of L-Hyoscyamine as an antispasmodic agent to relax and flatten any bulges or folds in or around a suspected lung lesion so that said lung lesion can be treated concomitantly with bronchoscopy.

16. The method of claim 1 whereby said oral formulation of L-Hyoscyamine is at least 0.125 mg and said at least one procedure of fine needle injection into a bronchial lesion/tumor is selected from endobronchial intratumoral chemotherapy and tumor ablation, said method further including the drying of secretions within a lung, said method providing improved direct visualization and advancement with a bronchoscope by alleviating obstruction in proximity to a lung lesion, said method further reducing/preventing reflex airway constriction, and said method further providing bronchodilation.

* * * * *